(12) United States Patent
Herman

(10) Patent No.: US 8,466,106 B2
(45) Date of Patent: Jun. 18, 2013

(54) NUCLEIC ACIDS ENCODING PEPTIDES FOR TREATING WOUNDS, ANTI-ANGIOGENIC COMPOUNDS AND USES THEREOF

(75) Inventor: Ira M. Herman, Newton, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 13/126,145

(22) PCT Filed: Oct. 27, 2009

(86) PCT No.: PCT/US2009/062187
§ 371 (c)(1),
(2), (4) Date: Apr. 26, 2011

(87) PCT Pub. No.: WO2010/062587
PCT Pub. Date: Jun. 3, 2010

(65) Prior Publication Data
US 2012/0178901 A1     Jul. 12, 2012

Related U.S. Application Data

(60) Provisional application No. 61/197,420, filed on Oct. 27, 2008.

(51) Int. Cl.
*A61K 38/18*     (2006.01)
*C12N 15/00*    (2006.01)
*C07H 21/04*    (2006.01)
*C07K 14/475*   (2006.01)

(52) U.S. Cl.
USPC ...... 514/13.3; 536/23.5; 435/320.1; 530/326; 530/328

(58) Field of Classification Search
None
See application file for complete search history.

(56) References Cited

U.S. PATENT DOCUMENTS
2007/0282095 A1   12/2007   Hosokawa

FOREIGN PATENT DOCUMENTS
| EP | 0637450 | 2/1995 |
| EP | 0852144 | 7/1998 |
| WO | WO 03/028543 | 4/2003 |
| WO | WO 2008/085794 | 7/2008 |

OTHER PUBLICATIONS

UniProtKB/TrEMBL Accession No. A4CP74. Apr. 3, 2007. [Retrieved from the internet on Apr. 13, 2010: <http://www.uniprot.org/uniprot/A4CP74.txt?version=1>].

*Primary Examiner* — Marianne P Allen
(74) *Attorney, Agent, or Firm* — Loeb & Loeb LLP

(57) ABSTRACT

The present disclosure relates to protein and peptide chemistry. More particularly, it relates to compounds, compositions and uses thereof for promoting and inhibiting angiogenesis. The peptides of the present disclosure include peptides comprising SEQ ID NOs: 1-4 which promote angiogenesis and cell proliferation. Further, the anti-angiogenic compounds of the present disclosure include antisense oligonucleotides that hybridize or are complementary to the polynucleotides of SEQ ID NOs: 5-16, and the like.

21 Claims, 4 Drawing Sheets

NUCLEIC ACIDS ENCODING PEPTIDES FOR TREATING WOUNDS, ANTI-ANGIOGENIC COMPOUNDS AND USES THEREOF

This application claims priority under 35 U.S.C. §119(e) to U.S. provisional patent application Ser. No. 61/197,420 filed on Oct. 27, 2008. The contents of the provisional application are hereby incorporated by reference in their entirety.

TECHNICAL FIELD

The present disclosure relates to protein and peptide chemistry. More particularly, it relates to compounds, compositions and uses thereof for promoting angiogenesis for wound healing and other aspects of regenerative medicine and inhibiting pathologic angiogenesis causing arthritis, complicating or compromising sight during aging (macular degeneration), diabetes (proliferative diabetic retinopathy) and responsible for tumor growth and metastasis.

BACKGROUND

It is widely recognized that the human body's response to injury is complex, and is dependent on a panoply of signaling pathways expressed by several cell and tissue types over an extended period of time. Importantly, the wound "bed" undergoes significant remodeling as re-epithelialization ensues concomitant with dermal angiogenesis. And, while wound healing typically occurs as a natural, uneventful process leaving the individual with neither noticeable scars nor wounds that chronically persist, this is not the case for 2-3% of the U.S. population. For these individuals, excessive scarring and chronic wounds are sustained as medical issues requiring specialized treatment, individualized care, or in some cases, hospitalization. Thus, while acute wound healing may occur in a matter of days or weeks, chronic wounds can remain in an open state for months and even years.

Under normal circumstances, the process of human wound healing can be broken down into three phases. An initial inflammatory phase, which is followed by robust tissue remodeling and proliferation (the proliferative phase), is ultimately succeeded by a "maturational phase" in which reepithelialization, dermal angiogenesis, and wound closure ensue. The inflammatory phase is characterized by homeostasis, with a provisional matrix contributed by the blood itself creating the initial wound bed. As basement membrane and interstitial collagens are exposed during injury, blood platelets are stimulated to release multiple chemokines, including epidermal growth factor (EGF), fibronectin, fibrinogen, histamine, platelet-derived growth factor (PDGF), serotonin, and von Willebrand factor, to name several. These factors help to stabilize the wound through clot formation and control bleeding, therein limiting the extent of injury. Platelet degranulation also initiates the complement cascade, specifically via C5a, which is a potent chemoattractant for neutrophils.

The timeline for cell migration in a normal wound-healing process is also well ordered, with an inflammatory phase beckoning the migration of immune response cells. For example, neutrophils function to decontaminate the wound from foreign debris via phagocytosis with support from immigrating macrophages. In turn, macrophages release cytokines that locally function to stimulate a robust proliferative response required for tissue morphogenesis and healing. It is during the proliferative phase that re-epithelialization and angiogenesis predominate. The entire process represents a dynamic and reciprocal continuum, with the angiogenesis of wound healing propagating and sustaining the re-epithelialization and tissue remodeling processes: all events continued until the wound site reaches maximal strength, perhaps as long as 1 year post-injury.

Throughout life, the vasculature undergoes significant morphogenesis. Two independent but related processes govern the formation of the adult vasculature: vasculogenesis and angiogenesis. Initially during vasculogenesis, immature vessels are formed de novo from endothelial cell precursors, the angioblasts, which proliferate and coalesce, creating a capillary plexus. Local differentiation of endothelial cells serves as an initiating event for the subsequent rounds of vascular "budding" or "sprouting," angiogenesis, which gives rise to the system of arteries, veins, arterioles, venules, and capillaries. Interestingly, in the adult, physiologic angiogenesis occurs during the female reproductive cycle, but otherwise the predominant form of physiologic angiogenesis during adult life occurs during wound healing.

Many positively and negatively acting factors influence the angiogenesis of wound healing, including the microenvironment in which vascular morphogenesis occurs. Soluble polypeptides, cell-cell and cell-matrix interactions, and hemodynamic and biomechanical forces all play strategic roles. More recently, we have learned that blood vessel sprouting during wound healing is likely to be critically dependent on a well-ordered signaling cascade responsible for regulating microvascular cytoskeletal function. In addition, clear-cut roles for the extracellular matrix and the repertoire of metalloproteinases controlling matrix remodeling also play modulatory roles in fostering wound-healing angiogenesis.

Investigations and procedures for examining and measuring healing, migration, and formation of new blood vessels that occur during the response to injury, and which are impaired during chronic wound healing during diabetes, venous stasis ulceration, pressure ulcer formation and ischemia-reperfusion disorders: all, are known in the art. See, for example, Demidova-Rice et al., Lasers in Surgery and Medicine 39:706-715 (2007); Kutcher et al., Am. J. Pathol. 171:693-701 (2007); Herman, et al., Stewart Martin, ed. (2007); Herman, D. Shepro, ed. Elsevier Pub, Inc. (2006); Riley et al., J. Burns & Wounds 4:141-59, (2005); Papetti et al., Am. J. Physiol 282:947-970, (2002); Papetti et al., Am. J. Pathol. 159:165-77 (2001); the disclosures of which are all incorporated herein by reference.

There is, therefore, a great interest and need in developing compositions and devices that are useful for treating wounds. See, for example, Gandy, U.S. Patent Publication No. 20080213238; Gandy U.S. Patent Publication No. 20060142198; Gandy U.S. Patent Publication No. 20060004189; Gandy U.S. Patent Publication No. 20050191286; and Gandy U.S. Patent Publication No. 20040197319, the disclosures of which are all incorporated herein by reference.

Other attempts to prepare wound healing compositions are disclosed in, for example, Knighton, U.S. Pat. Nos. 5,165,938 and 4,957,742, which disclose platelet enriched plasma produced from blood wherein the platelets are activated by thrombin which causes the release of platelet-derived growth and angiogenesis factors. A carrier, such as a microcrystalline collagen, is added to produce a wound-treating salve, and the composition is applied directly to wounds and initiates healing in non-healing wounds as well as accelerating normal wound-healing by increasing vascularization, stimulating fibroblast mitosis and migration, and increasing collagen synthesis by fibroblasts. It is said that the composition may also be applied to tissue to facilitate the growth of hair.

Worden, U.S. Pat. No. 6,524,568, discloses a platelet gel wound healing composition that includes growth factors and ascorbic acid and optionally including an antioxidant such as Vitamin A and/or Vitamin E. Antibiotics may also be included. Chao, U.S. Pat. No. 5,185,160, discloses a heat-treated, viral-inactivated platelet membrane microparticle fraction which may be prepared from outdated platelets. The microparticle fraction is said to be substantially free of platelet ghosts and may be used as a pharmaceutical preparation in transfusions. Chao, U.S. Pat. No. 5,332,578, also discloses a heat-treated, viral-inactivated platelet membrane microparticle product which may be prepared from outdated mammalian platelets. The microparticle product is said to contain isolated platelet membrane fragments that are free of alloantigens and GP IIb/IIIa complexes and it is said that the product may be used as a pharmaceutical preparation in transfusions.

Crowe, U.S. Patent Publication No. U.S. 2004/0265293A1, discloses a dehydrated composition that includes freeze-dried platelets. The platelets are loaded with trehalose in an amount from about 10 mM to about 50 mM, and at a temperature of from greater than about 25° C. to less than about 40° C. The freeze-dried platelets are said to be substantially shelf-stable and are rehydratable so as to have a normal response to an agonist, for example, thrombin, and it is said that virtually all of the platelets participate in clot formation within about three minutes at 37° C.

Van der Meulen et al., J. Membrane Biol. 71:47-59 (1983), discloses porcine alpha-granules that were found to be essentially homogeneous by transmission electron microscopy. Freeze-fractured samples of isolated granules revealed intramembranous particles on the exoplasmic fracture surface and, to a lesser extent, on the protoplasmic fracture surface, whereas the PS (protoplasmic) surface was relatively smooth and, it is said, the granules appeared to be sealed. Membranes were isolated by alkali extraction of the granules which removed protein and phospholipids yielding membrane vesicles devoid of the dense core. The membranes were said to contain major and minor polypeptides. The exposure of specific proteins on the cytoplasmic surface of the granule membrane was also determined. In sealed granules, bands were modified by the reagents, and a fraction eluted by alkali extraction was also analyzed and found to contain nine major polypeptides.

Chao et al., Transfusion 36:536-542 (1996), discloses preparation of IPM from outdated platelets. The platelets were disrupted by freezing and thawing, washed and heated to inactivate possible viral contaminants, and then a sonicated membrane microvesicle fraction was separated and lyophilized. The hemostatic activity of IPM was measured by its ability to reduce the prolonged bleeding time in thrombocytopenic rabbits. According to Chao, administration of IPM at a dose of 2 mg per kg results in a substantial reduction in the bleeding time. It is reported that, in a series of 23 experiments, a median preinjection bleeding time of 15 minutes was reduced to 6 minutes within 4 hours after IPM administration. Administration of IPM was said to show a mild enhancement in the thrombogenicity index, as measured in the Wessler rabbit model, which was not significant. Chao concludes that IPM may have clinical potential as a substitute for platelets in the treatment of bleeding due to thrombocytopenia.

Gogstad, Thrombosis Research 20:669-681 (1980), discloses a method for the isolation of alpha-granules wherein a two-step French pressure cell homogenization procedure produced an organelle concentrate for loading on density gradients. The procedure was said to be optimalized with respect to recovery of intact alpha-granules. The organelle homogenate was loaded to 17.5-27.5% metrizamide gradients and centrifuged. Organelle aggregate formation was said to be minimized by controlling the ionic conditions and the shape of the gradient. The alpha-granules were separated from lysosomes and dense bodies, but overlapped with the mitochondria, and the alpha-granules were recovered from the gradient to omit the major amount of mitochondria from the final preparation.

Hernandez, Vox Sang 73:36-42 (1997), discloses an investigation into the effects on hemostatsis of nonliving platelet derivatives. The effects of different platelet preparations on primary hemostatsis in a well-established perfusion model were evaluated, and studies were carried out with blood anticoagulated with low molecular weight heparin. Frozen-thawed, sonicated or lyophilized platelets were added to normal blood or to blood which had been experimentally depleted of platelets. Platelet interaction with the subendothelium and fibrin deposition were morphometrically evaluated. Hernandez reports that addition of non-viable platelet preparations to thrombocytopenic blood promoted a statistically significant increase in the deposition of fibrin on the subendothelium, but only lyophilized platelets retained some ability to interact with the subendothelium. Flow cytometry studies demonstrated the presence of GPIb, GPIIa and P-selection on lyophilized platelets. Hernandez concludes that preparations containing non-viable platelets may still retain some hemostatic properties.

Blood vessels are the method by which oxygen and nutrients are circulated and supplied to tissue, as well as the method by which waste products are removed from such tissue. Angiogenesis refers to the process by which new blood vessels are formed from preexisting blood vessels. See, for example, the review by Folkman and Shing, J. Biol. Chem. 267:10931-10934 (1992), Dvorak et al., J. Exp. Med. 174: 1275-1278 (1991). Accordingly, angiogenesis is generally considered an essential biological process, which includes instances where a greater degree of angiogenesis is desired, such as wound healing, as discussed above. However, abnormal or inappropriate angiogenesis, where there is excessive blood vessel proliferation, can lead to severe negative outcomes, as exemplified in vascularized ocular diseases such as proliferative diabetic retinopathy, and wet age-related macular degeneration and in cancers, where solid tumor growth has been demonstrated to be angiogenesis-dependent, with the newly developed or angiogenic microvessels transforming dormant avascular micrometastases into actively growing macroscopic tumors, which derive an ample supply of oxygen and nutrients from angiogenic tumor microvessels.

It is known that tumor growth impacts a large number of people each year, e.g., Cancer accounts for 7.1 million deaths annually (12.5% of the global total). Approximately 20 million people suffer from cancer; a figure projected to rise to 30 million within 20 years. The number of new cases annually is estimated to rise from 10 million to 15 million by 2020 (World Health Organization).

With respect to angiogenesis-dependent visually blinding disorders accompanying aging and diabetes, there is a comparably staggering and ever-increasing number of affected individuals. For example, with respect to visually blinding disorders observed during aging, angiogenic or vascular complications of AMD account for roughly 10 percent of all those patients suffering with AMD but, "wet" AMD accounts for 90 percent of all AMD-associated blindness: roughly 2.3 million of the 34 million Americans over age 70 will be affected. And, with respect to the visually blinding vascular complications associated with diabetes, it is likely that between 40 to 45 percent of Americans diagnosed with diabetes have some stage of diabetic retinopathy (www.nei.nih.gov).

Cancer is becoming an increasingly important factor in the global burden of disease. The estimated number of new cases annually is expected to rise from 10 million in 2000 to 15 million by 2020. Some 60% of these cases will occur in the less developed parts of the world. More than 7 million people now die each year from cancer. Yet with the existing knowledge, at least one-third of cancer cases that occur annually throughout the world could be prevented. The use of therapies designed to inhibit angiogenesis or neovascularization may significantly effect the growth of solid tumors and development of ocular disease. Through blocking angiogensis or neovascularization, tumor growth and ocular disease can be inhibited suggesting that these diseases require the continued blood vessel growth for progression of the tumors or ocular disease. Inhibition of angiogenesis or neovascularization is, therefore, a promising anti-cancer treatment and an anti-ocular angiogenic therapeutic approach as has recently been demonstrated (anti-VEGF).

Inhibition of angiogenesis may also be useful in treating diseases that are characterized by unregulated blood vessel development including, for example, vascular tumors (e.g., sarcomas, carcinomas, and lymphomas) and ocular diseases (e.g., macular degeneration and diabetic retinopathy). Cancer cells, as used herein, include tumors, tissue, and the like.

As can be seen from the above, there is a great need for and interest in developing compounds and compositions that are useful in treating and healing wounds, such as chronic wounds caused by diabetes which are difficult to heal. Not all current methods of treating chronic wounds have been successful. It is therefore an object of the present disclosure to identify new compounds and methods that will promote and improve wound healing, especially for chronic and otherwise unhealable wounds. Compounds and compositions that specifically promote keratinocyte migration to a wound, and which may not promote substantial keratinocyte proliferation, on the one hand, and which enhance endothelial cell formation, and which may not promote substantial endothelial cell migration or proliferation, would represent a significant advance over the products that are currently available for healing wounds. Further, there is great need for and interest in developing compounds and compositions that are useful in combating vascular tumors and certain vision-threatening complications resulting from abnormal angiogenesis, such as, for example, diabetic retinopathy or age-related macular degeneration. It is therefore another object of the present disclosure to identify novel compounds and compositions that inhibit abnormal angiogenesis, but do not ablate the complement of physiologic blood vessels or survival of normal cells and tissues that are required for normal organismic functionality. Disclosure of such approaches and/or entities would represent a significant advance over the current state of the art, standard of care or products that are currently available or are in use.

SUMMARY

In one object of the present disclosure, molecules or compounds and compositions for promoting angiogenesis through stimulation and growth of tissues and vascularization are provided. More particularly, the molecules, compounds, and compositions include the wound healing peptides and nucleic acid sequences described herein, which are isolated and purified or substantially purified. The molecules, compounds, and compositions comprising the wound healing molecules or compounds, may be used to treat insults to the body, such as burns, cuts, and scrapes; contusions, including oral and otolaryngological wounds; wounds that are caused and treated by plastic surgery; and bone damage.

Another object of the disclosure is directed to the wound healing peptides of SEQ ID NOs:1-4 and combinations thereof One object of the disclosure relates to the inventive composition comprising an effective amount of any one of or combination of the wound healing compounds, such as for example peptides of SEQ ID NOs: 1-4 and combinations thereof, described herein with a pharmaceutically- or physiologically-acceptable carrier, vehicle, or diluent. A therapeutic amount of the wound healing peptide of the disclosure is administered either directly or in a composition to a subject having a wound, including, for example, an acute accidental injury, surgical acute injuries, chronic wounds, ulcers, thermal injuries, combat casualty injuries, or a subject prone to hypertrophic scarring, such as keloid scarring. As used herein, "subject" refers to a mammal, including humans, horses, canines, felines, and the like.

In a further object, these wound healing compounds and compositions may be used alone or in combination therapy together with other growth promoting actives, such as isolated and purified or synthetically produced growth factors, and/or pain and inflammation reducing factors.

Another object of the present disclosure provides methods of using the wound healing compounds and compositions prepared, alone or in combination therapy. These wound healing compounds and compositions may be administered to a subject in need thereof in an amount effective to treat and/or heal a wound. Thus, the present disclosure also provides methods of treating subjects by administering to a subject in need thereof an effective amount of the wound healing compound or composition according to the disclosure as described herein. The present disclosure provides a particularly useful method of treating a patient suffering from diabetes or another disorder that prevents normal wound healing, or a subject being treated with a medication that prevents normal wound healing, by administering to the subject in need thereof an effective amount of a molecule or composition according to the instant disclosure.

A further object of the disclosure provides anti-angiogenic compounds, such as oligonucleotide sequences (also known as antisense oligonucleotides) that hybridize to or are complementary to the nucleotide sequences of SEQ ID NOs: 5-16 for treating a disease, disorder, or condition associated with abnormal neovascularization or angiogenesis.

One object of the disclosure relates to the inventive composition comprising an effective amount of any one of or combination of the anti-angiogenic compounds described herein (including antisense oligonucleotides of the disclosure) with a pharmaceutically- or physiologically-acceptable carrier, vehicle, or diluent.

A further object of the present disclosure provides a method for inhibiting angiogenesis, tumor growth and metastasis in the tissue of a subject or mammal in need thereof, by administering to the subject or mammal, an anti-angiogenic compound or composition comprising the anti-angiogenic compound, including for example, antisense oligonucleotides to any of the disclosed nucleotides, as described herein.

Further, in the methods of the present disclosure, a therapeutic amount of an anti-angiogenic compounds of the invention is administered to a human or other mammal having a disease or disorder/condition associated with abnormal neovascularization or angiogenesis, as described above.

Another object of the disclosure is a kit that includes elements for preparing and/or administering a wound treating molecule or composition. The kit includes a wound healing molecule or composition contained in a form to be applied to a wound, an applicator element for applying the wound healing molecule or composition to a wound, and optionally additional devices or materials useful for the preparation of the wound or administration of the wound healing molecule or composition.

Yet another object of the disclosure is a kit that includes elements for preparing and/or administering an anti-angiogenic compound of the present disclosure. The kit includes an anti-angiogenic compound contained in a form to be administered to a subject, and optionally additional devices or materials useful for administration of the anti-angiogenic compound.

These and other aspects of the present disclosure will become apparent to those skilled in the art after a reading of the following detailed description, including the illustrative embodiments and examples.

DETAILED DESCRIPTION

Peptides and Nucleic Acids

Figure 1:
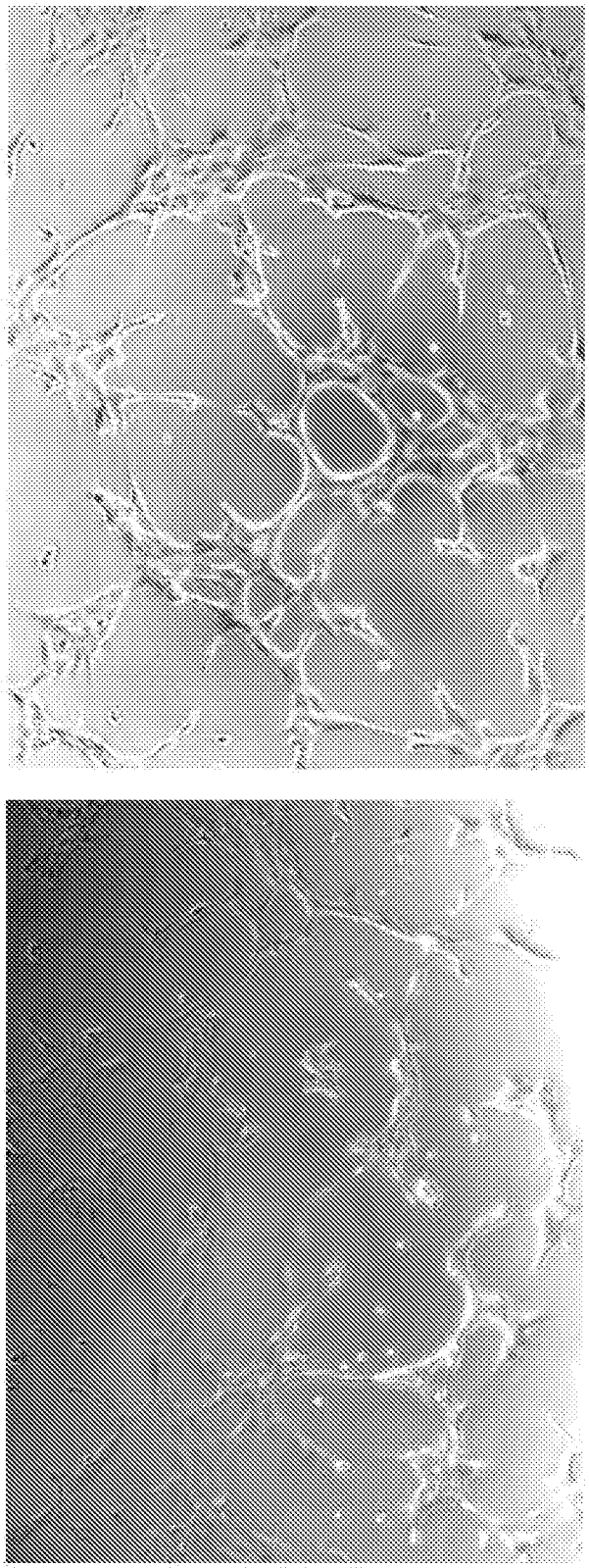
FIG. 1 is an illustration of a comparison 0.5 nM of the peptide of SEQ ID NO: 1 ("UN1") to a serum control sample in the formation of tubules from Human Microvascular Endothelial Cells (HMVEC) in Matrigel™ after 3 hours. The number and lengths of the processes or tubules formed after the addition of 0.5 nM of the peptide of SEQ ID NO: 1 shows significant induction of in vitro angiogenesis compared with the control.

Embodiments of the instant disclosure include compounds, compositions and uses thereof for promoting and inhibiting angiogenesis. These wound healing and anti-angiogenic compounds may be used in the treatment of wounds and abnormal vascular diseases, including for example, cancers. Anti-angiogenic compounds encompass compounds used for anti-vascularization, anti-proliferation, and the like. Additionally, aspects of the instant disclosure are useful for diagnostic assays.

One embodiment of the disclosure provides isolated or purified peptides of SEQ ID NOs: 1-4 as wound healing compounds. As is known, peptides are formed by linking of amino acids through peptide bonds. Peptides are made up of only a few amino acids; whereas proteins generally have greater than 50 amino acid residues.

The peptides of the disclosure may be prepared in any suitable manner. Such peptides include isolated naturally occurring peptides, recombinantly produced peptides, synthetically produced peptides, or peptides produced by a combination of these methods. The means for preparing such peptides are well understood in the art. The peptides may be a part of a larger protein, such as a fusion protein. The inclusion of additional amino acid sequence which contains secretory or leader sequences, pro-sequences, sequences which aid in purification, such as multiple histidine residues, or an additional sequence for stability during recombinant production is also advantageous.

A further embodiment of the disclosure relates to peptides that are in an isolated form and substantially purified. A recombinantly produced version of a peptide can be substantially purified using techniques described herein or otherwise known in the art, such as, but not limited to, for example, by Affinity Chromatography, Ion Exchange Chromatography, Hydrophobic Interaction Chromatography, Gel Filtration, Reversed Phase Chromatography, and the like. Peptides of the invention also can be purified from natural, synthetic or recombinant sources known in the art.

In another embodiment, peptides of the present disclosure are composed of amino acids joined to each other by peptide bonds or modified peptide bonds, i.e., peptide isosteres, and may contain amino acids other than the 20 gene-encoded amino acids. The peptides may be modified by either natural processes, such as posttranslational processing, or by chemical modification techniques which are well known in the art. Such modifications are detailed in basic texts, as well as in the vast research literature.

Modifications can occur anywhere in a peptide, including the peptide backbone, the amino acid side-chains and the amino or carboxyl termini. It will be appreciated that the same type of modification may be present in the same or varying degrees at several sites in a given peptide. Any given peptide may contain multiple types of modifications. For example, the peptides may be branched, as a result of ubiquitination, and they may be cyclic, with or without branching. Cyclic, branched, and branched cyclic peptides may result from natural posttranslational processes or may be made synthetically. Non-limiting modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Structure in Protein Chemistry*, 2$^{nd}$ Ed. Jack Kyte, Taylor & Francis, Inc., New York (2006); *Proteins—Structure and Molecular Properties*, 2$^{nd}$ Ed., T. E. Creighton, W. H. Freeman and Company, New York (1993); *Posttranslational Covalent Modification of Proteins*, B. C. Johnson, Ed., Academic Press, New York, pgs. 1-12 (1983).

The peptides may be combined in different combinations and orders. For example, the peptides of SEQ ID NOs: 1 and 2 are linked, from N-terminus to C-terminus, with a linker, for example, proline ("Pro") to create SEQ ID NO: 3. The two peptides can be linked with any amino acid or artificial synthetic molecule that would enable attachment of the two peptides. Another embodiment is the peptides of SEQ ID NOs: 1 and 2 are linked, from N-terminus to C-terminus, with a linker, for example, proline ("Pro") to create SEQ ID NO: 4. Peptides of the disclosure encompass any of the peptides, in any order, in any combination. For example, an embodiment of the present disclosure could be: [SEQ ID NO: A]$_m$-X-[SEQ ID NO: B]$_n$, where "A" and "B" are different sequences disclosed herein, "X" is a linker (e.g., proline), and "m" and "n" are any positive integer including zero except that m and n cannot be simultaneously be zero.

The compounds of the present disclosure may be isolated and purified by techniques known in the art. Example 1 describes the isolation and identification of the inventive peptides. Techniques include, such as, for example, by solubility, size, charge, hydrophobicity, and by affinity. The wound healing and anti-angiogenic compounds used in compositions of the disclosure not only comprise of a pharmaceutically- or physiologically-acceptable carrier, but also optionally, any other component that may seem fit for the benefit of the intended purpose of wound healing.

A further embodiment of the disclosure provides a polynucleotide comprising, or alternatively consisting essentially of or consisting of, the sequence identified in or a polynucleotide of any one of SEQ ID NOs: 5-16. Yet another embodiment relates to polynucleotides encoding the peptides of the disclosure comprising, or alternatively consisting essentially of or consisting of, the peptide sequences of SEQ ID NOs: 1-4. The polynucleotide sequence of SEQ ID NOs: 5, 9, and 13 encode each of the amino acid sequences or peptides of SEQ ID NOs: 1, 2, and 3, respectively. The polynucleotide sequences can be synthesized in a number of different ways, such as for example, reverse translation. Furthermore, where wobble nucleotide positions are possible, multiple nucleotides capable of encoding each peptide/protein are provided. Thus, for the amino acid sequence of SEQ ID NO: 1, the corresponding nucleotide sequences are SEQ ID NOs: 5-8. For the amino acid sequence of SEQ ID NO: 2, the corresponding nucleotide sequences are SEQ ID NOs: 9-12. For the amino acid sequence of SEQ ID NO: 3, the corresponding nucleotide sequences are SEQ ID NOs: 13-16.

| LIST OF SEQ ID SEQUENCES | |
|---|---|
| SEQ ID NO: 1 | GluLeuLeuGluSerTyrIleAspArg |
| SEQ ID NO: 2 | ThrAlaThrSerGluTyrGlnThrPhePheAsnProArg |
| SEQ ID NO: 3 | GluLeuLeuGluSerTyrIleAspArgProThrAlaThrSerGluTyrGlnThrPhePheAsnProArg |
| SEQ ID NO: 4 | ThrAlaThrSerGluTyrGlnThrPhePheAsnProArgProGluLeuLeuGluSerTyrIleAspArg |
| SEQ ID NO: 5 | GAACTTCTTGAATCTTATATTGATCGT |
| SEQ ID NO: 6 | GAGTTCTTCGAGAGCTACATCGACAGC |
| SEQ ID NO: 7 | GAACTACTAGAATCATATATAGATCGA |
| SEQ ID NO: 8 | GAACTGCTGGAATCGTATATTGATCGG |
| SEQ ID NO: 9 | ACTGCTACTTCTGAATATCAAACTTTTTTAATCCTCGT |
| SEQ ID NO: 10 | ACCGCCACCAGCGAGTACCAGACCTTCTTCAACCCCAGC |
| SEQ ID NO: 11 | ACAGCAACATCAGAATATCAAACATTTTTTAATCCACGA |
| SEQ ID NO: 12 | ACGGCGACGTCGGAATATCAAACGTTTTTTAATCCGCGG |
| SEQ ID NO: 13 | GAACTTCTTGAATCTTATATTGATCGTCCTACTGCTACTTCTGAATATCAAACTTTTTTAATCCTCGT |
| SEQ ID NO: 14 | GAGTTCTTCGAGAGCTACATCGACAGCCCCACCGCCACCAGCGAGTACCAGACCTTCTTCAACCCCAGC |
| SEQ ID NO: 15 | GAACTACTAGAATCATATATAGATCGACCAACAGCAACATCAGAATATCAAACATTTTTTAATCCACGA |
| SEQ ID NO: 16 | GAACTGCTGGAATCGTATATTGATCGGCCGACGGCGACGTCGGAATATCAAACGTTTTTTAATCCGCGG |

In another embodiment, the polynucleotides of the present disclosure may be composed of any polyribonucleotide or polydeoxribonucleotide, including modified RNA or DNA or unmodified RNA or DNA. For example, polynucleotides may comprise single- and double-stranded DNA, single- and double-stranded RNA, DNA that is a mixture of single- and double-stranded regions, and RNA that is mixture of single- and double-stranded regions, hybrid molecules comprising DNA and RNA that may be single-stranded or, more typically, double-stranded or a mixture of single- and double-stranded regions. Additionally contemplated are polynucleotide that are comprised of triple-stranded regions or RNA or DNA or both RNA and DNA. A polynucleotide may also contain one or more modified bases or DNA or RNA backbones modified for stability or for other reasons. Modified bases include, for example, methylated or tritylated bases and unusual bases such as inosine. DNA and RNA may be made modified in a variety of ways. Hence, polynucleotides of the instant disclosure also embrace chemically, enzymatically, or metabolically modified forms.

DNA shuffling, which includes but is not limited to, gene-shuffling, motif-shuffling, exon-shuffling, and codon-shuffling, are techniques useful in generating fusion proteins of the disclosure. The activities of peptides and polypeptides of the disclosure may be modulated or altered by using the DNA shuffling technique to generate agonists or antagonists of the peptides or polypeptides. See, for example, U.S. Pat. Nos. 5,605,793; 5,811,238; 5,830,721; 5,834,252; and 5,837,458, and Patten et al., *Curr. Opinion Biotechnol.* 8:724-33 (1997); Harayama, *Trends Biotechnol.* 16(2):76-82 (1998); Hansson, et al., *J. Mol. Biol.* 287:265-76 (1999); and Lorenzo and Blasco, *Biotechniques* 24(2):308-13 (1998).

In one embodiment, the inventive polynucleotides disclosed herein that correspond to SEQ ID NOs: 5-16 and the peptides encoded by these polynucleotides may be attained by DNA shuffling. The assemblage of two or more DNA segments by homologous or site-specific recombination may generate variation in the polynucleotide sequence by DNA shuffling. Another embodiment relates to the polynucleotides of the invention, or the encoded peptide or polypeptides, that may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a peptide or polypeptide of the invention may be recombined with one or more components, motifs, sections, parts, domains, fragments, etc. of one or more heterologous molecules.

Formation of an Expression Vector

An expression vector of the present disclosure is a vector containing at least one of the polynucleotides of SEQ ID NOs: 5-16 as described above. A DNA vector of the present invention may be prepared by ligating a plasmid DNA having an artificial nucleotide sequence to the DNA molecule of the present invention. For example, the DNA of interest may be inserted into the vector by using two different restriction enzymes for cutting both the vector and insert, and then ligating the ends. However, when the ends are blunt ends, a linker may be utilized to facilitate the ligation and insertion of the DNA of interest. The linker is at least one or two more nucleotide(s) that is/are not naturally connected to the DNA molecule of the present invention, and is appropriately designed depending on the site of the vector to be inserted.

Non-limiting examples of expression vectors, including DNA vectors in which the DNA molecule of the present invention is integrated, include a plasmid such as pBR322, pBR325, pUC7, pUC8, pUC18, pUC19, pBluescript or pGEM; a cosmid such as pHC79; and a phage such as pUC19, or M13 phage. The vector is digested with appropriate restriction enzymes and the DNA molecule disclosed herein with or without additional sequence, such as linker, is inserted therein by standard molecular procedure known and understood by the scientist.

A DNA vector to construct the expression vector for a polynucleotide encoding peptide of Sequence ID Nos. 1-3 is not limited, and may be chosen from any of the aforesaid vectors or those known in the art. A DNA vector to express the objective protein as a fusion protein with a Tag, by which the objective protein could be affinity-purified, is more suitable. For examples of such a vector, pGEX vector (AMERSHAM BIOSCIENCES Corp.) or pQE vector (QIAGEN Inc.) is commercially available.

The transcriptional regulation region, comprising a promoter and a terminator, is necessary for inclusion in the expression vector. The suitable promoter differs in host-by-host cell. For example, lac, tac or T5 promoter is used as promoter in the case of $E.\ coli$ as host cell. OAX1 or GAPDH promoter in the case of yeast, polyhedrin promoter in the case of insect cell, or CMV or $\beta$-actin promoter in the mammalian cells are suitable.

Host Cell

Using the resulting expression vector as described above, a variety of host cells can be appropriately transformed to obtain a microorganism or cells capable of producing the peptides of SEQ ID NOs: 1-4 or a recombinant protein comprising a part of any of SEQ ID NOs: 1-4 and a Tag sequence. The appropriate transformation methods are well known to one skilled in the art.

Host cells used herein can be selected in terms of compatibility of the expression vector, suitability of the products, etc., and may be either prokaryotic or eukaryotic cells. Specific examples of host cells include, but are not limited to, bacteria such as the genus $Escherichia$ (e.g., $E.\ coli$) or the genus $Salmonella$ (e.g., $Salmonella\ typhimurium$), and lower eukaryotic cells such as yeast (e.g., $Saccharomyces\ cerevisiae$) or fungi (e.g., $Penicillium$). Non-limiting examples of host cells in higher eukaryotic cells are insect cells, Chinese hamster ovary (CHO) cells, CEF cells, or human cell lines (e.g., HeLa).

Expression of the Wound Healing Peptide

Host cells transformed with an appropriate expression vector can be cultured and proliferated under incubation conditions well known to one skilled in the art.

For example, the transformed $E.\ coli$ can be well grown in LB medium at 37° C., under aerobic conditions. In producing a peptide of the present invention, the condition for the induction of the protein can be chosen according to the used promoter. In the case of $E.\ coli$ lactose promoter and operator system, as a specific example, it is achieved by adding an appropriate amount of isopropyl-1-thio-$\beta$-D-galactopyranoside (IPTG) to a culture medium.

A method to purify the peptides of the invention is not particularly limited, and any known method is applicable to the purification in combination with techniques well known in this field. When the peptides of the invention are expressed as a fusion protein containing some Tag that can be used in purification through an affinity column, the affinity column is a very convenient tool. For example, the peptides of the invention expressed as fusion with glutathione S-transferase (GST) using pGEX vector could be purified easily through Glutathione Sepharose 4B column (AMERSHAM BIOSCIENCES Corp). Thus, in another embodiment, the present disclosure includes a prokaryotic or eukaryotic host cell transformed or transfected with a DNA sequence as described above in a manner allowing the host cell to express the polypeptide.

Viral Transduction in Situ—Peptide Adenovirus Construction

The coding sequence for the peptides of the disclosure can be cloned into an appropriate vector, such as a pEF-BOS vector, into, for example, pAdTrack-CMV, to take advantage of a forward primer containing restriction sites that would enable tagging the peptide with a definitive expression tag, if needed, e.g., a KpnI site, a Kozak consensus site, and a region targeting a myc sequence (5'GCGGTTACCACCACCATG-GAACAAAAACTCATCTCAGAA-3') (SEQ. ID NO: 17), whereas a reverse primer containing an XbaI restriction site, for example, and a region complementary to the peptide(s) 3' sequence.

The peptide-pAdTrack-CMV construct, confirmed by restriction digestion and DNA sequencing, can then be linearized with PmeI and co-transformed with the pAdEasy-1 adenoviral backbone into $E.\ coli$ BJ5183 and selected for kanamycin resistance. The resulting recombinant plasmid can then be transfected into the 293 packaging cell line and the resultant Ad-peptide adenoviral construct, e.g., an Ad5 serotype deleted for E1 and E3, or a related adeno-associated virus, can then be amplified and purified using CsCl density gradient centrifugation. Adenoviral titer can then be determined by using standard assays before use in vitro or in vivo. In this way, regulated expression of peptide(s) can be delivered on demand and in situ (e.g., a wound bed with a chronic inability to heal wounds because of failed angiogenesis).

Anti-Angiogenic Compounds

Another embodiment is directed to compounds, compositions, and methods for inhibiting angiogenesis, tumor growth, ocular disease or any other disease or condition that is characterized or associated with abnormal angiogenesis or pathologic neovascularization. Although, as described above, angiogenesis is important to make new blood vessels, for example, to heal wounds and repair damage, as is known, pathologic angiogenesis represents a critical step in tumor progression through which the tumor develops an autonomous blood supply, thus facilitating tumor growth. See, for example, Hanahan et al., Cell 100:57-70 (2000); Bergers et al., Nat. Rev. Cancer 3:401-410 (2003). However, the creation of very small blood vessels give a tumor its blood supply and allow it to be viable and grow. Anti-angiogenesis treatment is, therefore, a useful means for targeting tumors and cutting off their blood supply, without which tumors cannot grow. Without being bound by theory, these anti-angiogenic compounds may or may not target the cancer cells and cancer stem cells specifically, but it is more likely that they target the blood vessels supplying the cancer cells. In addition, other diseases that are characterized by unregulated blood vessel development including but not limited to, for example, ocular diseases (e.g., macular degeneration and diabetic retinopathy) are dependent upon angiogenesis or neovascularization, and may also benefit from the anti-angiogenesis therapy described herein.

Further, the methods of the present disclosure provide anti-angiogenic compounds that inhibit the formation of new blood vessels (angiogenesis or neovascularization) required to establish and sustain tumors or the vascular complications of visually blinding disorders as is seen in aging and diabetes. The present invention additionally provides methods and compositions that directly inhibit tumor growth, ocular disease, and other diseases or conditions associated with abnormal angiogenesis or neovascularization.

Diseases, disorders, or conditions associated with abnormal neovascularization or angiogenesis include, but are not limited to, retinal neovascularization, hemagiomas, solid tumor growth (including sarcomas, lymphomas and carcinomas), metastasis, neovascular glaucoma, diabetic retinopathy, endometriosis, macular degeneration and retinopathy of prematurity (ROP). As used herein, the term "neovascularization" refers to the growth of blood vessels and capillaries, and "angiogenesis," as discussed above, refers to the physiological process by which new blood vessels develop from pre-existing vessels. Normal angiogenesis is physiologic; abnormal angiogenesis is pathologic.

Through the inhibition of angiogenesis, one can intervene in the progression or development of disease, ameliorate symptoms, or cure disease. Where the production of new blood vessels is required for the continued growth of abnormal tissue (e.g., cancer tissue), inhibiting angiogenesis will impede the blood supply to the abnormal tissue and, thus, reduce tissue mass due to lack of nutrients and oxygen being delivered to the abnormal tissue. Examples include cancerous tumors, proliferative diabetic retinopathy, inflammatory diseases, retinosis, macular degeneration, or any abnormally vascularized disease, condition or disorder, among others. The methods of the present disclosure are effective in part because the therapy is selective for angiogenesis.

Another embodiment of the disclosure is directed to anti-angiogenic compounds that hybridize, recognize or bind to SEQ ID NOs: 5-16. These anti-angiogenic compounds may successfully inhibit the pathologic angiogenesis accompanying tumor growth when delivered systemically or the neovascularization that takes place as a vision-threatening complication of diabetic retinopathy or age-related macular degeneration when delivered locally into the vitreal or intra-retinal compartment. As discussed above, the present disclosure of peptides and nucleic acids for the purpose of wound healing promotes angiogenesis. Accordingly, by inhibiting angiogenesis, antisense oligonucleotides act in the reverse of the wound healing actions of the peptides.

The peptides of the disclosure also include peptides that are biologically and/or immunologically active. The activity of these peptides can refer to a biological function (either inhibitory or stimulatory), such as but not limited to the promotion of cell migration to a wound and cell proliferation of the cells that lead to healing of a wound or heal a wound. The peptides of the disclosure may be used for diagnostic purposes. For example, the peptides may be used to detect angiogenesis. Example 2 further exemplifies such a diagnostic use.

Just as the peptides of the present invention (SEQ ID NO: 1 and SEQ ID NO: 3) have been shown to induce angiogenesis in vitro and promote keratinocyte migrations in response to injury in vitro, immunizing rabbits with SEQ ID NO: 1 and SEQ ID NO: 3 also elicits an immune response generating polyclonal anti-angiogenic compounds.

Antisense Oligonucleotide Sequences

Another embodiment of the instant disclosure includes a nucleic acid sequence which hybridizes with a DNA or nucleotide sequence of SEQ ID NOs: 5-16, the complement thereof, or the cDNA under stringent conditions. These antisense oligonucleotides or nucleic acid sequences that are purified and isolated sequences are useful in inhibiting abnormal angiogenesis or neovascularization. The hybridizing polynucleotides have at least about 70% sequence identity; at least about 80% identity; at least about 90%; or at least about 95% identity with the polynucleotide of the present disclosure to which they hybridize, where sequence identity is determined by comparing the sequences of the hybridizing polynucleotides when aligned so as to maximize overlap and identity while minimizing sequence gaps. The methods of determining percent identity are commonly known in the art.

Stringent hybridization conditions refers to an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1× SSC at about 65° C.

These antisense oligonucleotides or nucleic acid molecules or sequences are also contemplated to hybridize to the polynucleotides of the present disclosure under lower stringency hybridization conditions. By manipulating the formamide concentration (lower percentages of formamide result in lowered stringency); salt conditions, or temperature, the stringency of hybridization and signal detection may be altered. For example, lower stringency conditions include incubating overnight at 37° C. in a solution comprising 6×SSPE (20× SSPE=3M NaCl; 0.2M $NaH_2PO_4$; 0.02M EDTA, pH 7.4), 0.5% SDS, 30% formamide, 100 ug/ml salmon sperm blocking DNA; followed by washing at 50° C. with 1×SSPE, 0.1% SDS. The ordinarily skilled artisan understands that to achieve even lower stringency, multiple washes can be performed at higher salt concentrations (e.g. 5×SSC) following stringent hybridization.

Variations in the above conditions may be accomplished by adding or substituting alternate blocking reagents used for suppressing the undesirable background in hybridization experiments. Typical blocking reagents include, but are not limited to, Denhardt's reagent, BLOTTO, heparin, denatured salmon sperm DNA, and commercially available proprietary formulations. As understood in the art, the hybridization conditions described above may require modification of certain blocking reagents due compatibility issues.

Thus, the present disclosure includes purified or isolated DNA sequences encoding any of the peptides of SEQ ID NOs: 1-4, the DNA sequence being selected from the group consisting of (a) the DNA sequences set out in SEQ ID NOs: 5-16 or their complementary strands; and (b) nucleic acid sequences which hybridize under stringent conditions to the DNA sequences defined in SEQ ID NOs: 5-16. The purified or isolated DNA sequence may consist essentially of a DNA sequence encoding a polypeptide having an amino acid sequence sufficiently duplicative of that of any of the peptides of SEQ ID NOs: 1-4 to allow possession of the biological property of causing angiogenesis tube formation, cell migration or proliferation, and/or keratinocyte migration or proliferation. Further, the nucleic acid will be a functional peptide selected from SEQ ID NOs: 1-4. The DNA sequence may be a genomic DNA sequence, but will preferably be a cDNA sequence.

It has been shown that the effectiveness of these nucleic acid sequences that hybridize to the polynucleotide sequences of interest or antisense sequences may be beneficially modified to increase their stability in vivo through modification of the backbone (including 2'-MOE (2'-O-2-methyloxy(ethyl)) modification, creating a phosphorothioate backbone (replacing the non-binding phosphoryl oxygen atom with a suffer atom), or methylation of amino acids, such as but not limited to cytosines and uracils. See, for example, Gleave et al., U.S. Pat. No. 6,900,187; Bennett et al., U.S. Pat. No. 6,111,094; Monia et al., J. Biol. Chem. 268:14514-14522 (1993); Miyake et al., Clin. Cancer Res. 6:1655-1663 (2000); Miyake H et al., Expert Opinion on Investigation Drugs 15:507-517 (2006); Monia et al., J. Biol. Chem. 268:14514-14522 (1993); and Zellweger et al., J. Pharm. And Exp'l Therapeutics 298:934-940 (2001).

APPLICATIONS

In one embodiment, the wound healing molecules and compositions of the present disclosure can promote stimulation and growth of tissues including epithelial tissue, which further includes simple or stratified squamous, cuboidal and columnar epithelial tissue; connective tissue such as loose or dense, cartilage, adipose, bone, and blood connective tissue (e.g., angiogenesis which occurs during wound healing); can be used for promoting stimulation and growth of muscle tissue such as voluntary and involuntary, striated and smooth, and cardiac muscle tissue; and nervous tissue such as central nervous system (CNS) tissue, which is comprised of the brain and spinal cord, and the peripheral nervous system (PNS) tissue, which is comprised of all the other nervous tissue in the body. The molecules and composition may also be used for organ regeneration, reducing scarring, for cosmetic applications, such as, cosmetic surgery, treating sun-damaged skin, wrinkles, promoting hair growth, as a haemostatic agent, or as a medium for growth of cells and cultures. Types of wounds that may be treated include partial and full-thickness wounds; pressure ulcers; venous ulcers; chronic vascular ulcers; diabetic ulcers; civilian or military trauma wounds (abrasions, lacerations, second-degree burns, skin tears); drainage wounds and surgical wounds (donor sites/grafts, post-Mohs' surgery, post-laser surgery, podiatric, wound dehiscence). More particularly, the molecules and compositions of the present invention can promote keratinocyte migration to a wound and enhance endothelial cell formation.

As used herein, the term "composition" is intended to mean at least one or a plurality of components, elements or molecules of the aforementioned types, such as but not limited to, the wound healing peptides or polypeptides, the polynucleotides encoding the wound healing peptides or polypeptides, the oligonucleotides that hybridize to or are complementary to the polynucleotides of the instant disclosure, and the like, directed against the wound healing peptide or polypeptides of the disclosure, and the like with a carrier, vehicle, or diluent. The compositions of the disclosure may optionally contain growth factors in isolated and/or purified form, as well as synthetic growth factors. Non-limiting examples of useful growth factors in the composition include one or more of any of the following: PDGF-AA, PDGF-BB, PDGF-AB, EGF, VEGF, TGF-alpha, FGF, TGF-beta, IGF-1, IGF-2, NGF, and erythropoietin, and/or cytokines generally, and/or lymphokines generally, and/or interleukins, and/or monokines. As used herein (and described below), percentages are based on the weight of the composition.

Preferably, the composition will comprise of or consist essentially of only components that do not alter the basic novel characteristics of promoting cell migration to a wound and cell proliferation of the cells that lead to healing of a wound and/or heal a wound. The disclosed composition may therefore comprise or consist essentially of one or more of the foregoing molecules and/or factors. However, one embodiment of the disclosure is directed to a composition that excludes components having de minimus, or are nonessential, or no effect on the basic and novel characteristics of the wound healing ability of the components of the composition. In another embodiment, the disclosed compositions exclude components that have de minimus, or are nonessential, or no effect on the basic and novel characteristics of the anti-angiogenesis characteristics of those particular components useful for such purposes.

When a composition includes growth factors, in terms of nanograms per milliliters, the growth factors may be included in an amount of from about 10 ng/ml to about 500 ng/ml growth factors, more preferably from about 40 ng/ml to about 300 ng/ml growth factors, and most preferably from about 90 ng/ml to about 220 ng/ml growth factors. Preferably, the growth factors will be platelet derived growth factors (PDGF) or vascular endothelial growth factor (VEGF).

Further examples of wound healing and/or repairing and/or growth promoting agents that may be combined with or used in combination with the compounds according to the present disclosure may include porcine derived agents such as OASIS™ manufactured by Cook Biotech Incorporated and distributed by Healthpoint, Ltd., San Antonio, Tex.; or one or more carriers or vehicles, e.g., purified water, glycerin, carboxymethyl cellulose, sodium, allantoin, benzyl alcohol, methylparaben, propylparaben, each of which is found in SoloSite™, by Smith and Nephew, Largo, Fla. The wound healing compounds may also be used in conjunction with scaffolds to assist in the angiogenesis and wound healing.

In embodiments wherein one or more additional growth promoting active agents, one or more antibacterial agents, one or more pain relievers, one or more vitamins, one or more minerals, and/or one or more herbal factors are included, the composition will include an effective amount of the one or more of the molecules according to the invention, an effective amount of the one or more additional growth promoting active agents, an effective amount of the one or more antibacterial agents, an effective amount of the one or more pain relievers, an effective amount of the one or more vitamins, an effective amount of the one or more minerals, and an effective amount of the one or more herbal additives.

Examples of suitable carriers and/or vehicles, such as pharmaceutically acceptable carriers, include one or more of collagen, such as microcrystalline collagen, creams, microcapsules, oils, aloe vera, a wax, a polyol, one or more fats or oils, one or more emulsifying agents, and/or one or more water-soluble gums, water, saline, stearyl alcohol NF, white petrolatum USP, polyoxyl 40, stearate NF, carboxymethyl cellulose, lanolin, alginate, such as calcium alginate, gel, propylene glycol USP, isopropyl myristate NF, and/or sorbitan monooleate NF with 0.3% methylparaben NF. The composition may optionally include a preservative. The carrier and/or vehicle may be included in the composition in an amount from about 1% to about 99% of the composition, preferably from about 25% to about 50%, most preferably from about 30% to about 40% of the total composition or combination.

Examples of suitable additional growth promoting active agents include epidermal growth factors, steroids, enzymes, and hormones, natural (such as having been isolated and purified) or synthetic. The additional growth promoting active agents may be included in the composition in an amount of from about 1% to about 50% of the composition.

Examples of suitable antibacterial agents that may be applied before, during, or after treatment with the composition as a solution or a cream, gel, or a paste, include silver compounds, such as silver nitrate, honey, sulfamylon, silver sulfadiazine, such as a micronized silver sulfadiazine cream (e.g., THERMAZENE™ by Kendall, Mansfield, Mass.), saline; neosporin, and/or a mycin, such as vancomycin, gintamycin, erythromycin or derivative, and/or a cillin, such as a penicillin, or amoxicillin. Other antimicrobial agents include iodine, such as beads of cadexomer iodine found in IODOSORB™ GEL, by Healthpoint™, San Antonio, Tex. The antibacterial agents may be included in the composition in an amount of from about 1% to about 25% of the composition.

The compounds and compositions of the present invention can also be combined with commercially available wound repairing or healing dressings, such as, for example, a sodium chloride dressing (e.g., Mesalt™ by Molnlycke Health Care AB, Goteborg, Sweden), a silver antimicrobial dressing (e.g., SilvaSorb™ by AcryMed, Inc., Portland, Oreg. and Acticoat* or Acticoat*7 by Smith & Nephew, Inc., Largo, Fla.), a silver impregnated antimicrobial dressing (e.g., Aquacel™ by ConvaTec Limited, Division of E. R. Squibb and Sons, Inc., Princeton, N.J. and Maxorb™ by Medline Industries, Inc., Mundelein, Ill.), a sodium alginate silver oxide dressing, optionally containing sustained-release polymers that dissolve in water releasing silver ions into the wound (e.g., Argiaes™ Powder by Medline Industries, Inc., Mundelein, Ill.), a hydrocolloid dressing, optionally containing an inner wound contact layer of hydrocolloids contained within an adhesive polymer matrix and an outer layer of polyurethane film (e.g., SignaDress™ DuoDerm™ by ConvaTec Limited, Division of E. R. Squibb and Sons, Inc., Princeton; N.J.), a collagen and/or calcium alginate dressing (e.g., Fibracol™ by Johnson and Johnson Medical, Skipton, United Kingdom and AlgiSite* M by Smith & Nephew, Inc., Largo, Fla.), a dressing layer containing soft silicone (e.g., Mepitel™ by Molnlycke Health Care AB, Goteborg, Sweden), a dressing containing polyhexamethylene biguanide and/or cellulose (e.g., XCell™ by XYLOS Corporation, Langhorne, Pa.), a dressing containing hyaluronic acid or an ester of hyaluronic acid (e.g., Hyaff™, Hyalofill™ F, or Hyalofill™ R by ConvaTec Limited, Division of E. R. Squibb and Sons, Inc., Princeton, N.J.), a dressing made of sponge, optionally containing hydrofera bacteriostatic polyvinyl alcohol sponge (e.g., Hydrofera Blue™ by Hydrofera™, Willimantic, Conn.), and/or a dressing or pad containing spherical hydrophilic beads of cadexomer, optionally containing iodine and/or polyethylene glycol (e.g., Iodoflex™ Pad by Healthpoint, Ltd., San Antonio, Tex.).

The compounds and compositions of the present invention can further be combined with commercially available wound repairing or healing ointments, such as, for example, an ointment containing papain, which is derived from papaya (e.g., Panafil™ or Accuzyme™ by Healthpoint, Ltd., Forth Worth, Tex.).

The compounds and compositions of the present invention can also be combined with commercially available wound repairing or healing gels, such as, for example, a sodium chloride gel (e.g., Hypergel™ by Molnlycke Health Care AB, Goteborg, Sweden); and/or gels containing one or more of the following ingredients water, glycerin, glycereth-7, polyvinylpyrrolidone, carbomer, triethanolamine, EDTA, propylene glycol, diazolidinyl urea, methylparaben, and propylparaben, such as found together in 3M™ Tegagel™ Hydrogel Wound Filler by 3M Heath Care, St. Paul, Minn.

The compounds and compositions of the present invention can further be combined with commercially available wound repairing or healing sprays, such as, for example, a spray containing papain (e.g., Panafil™ Spray by Healthpoint, Ltd., Forth Worth, Tex.).

The compounds and compositions of the present invention can further be combined with commercially available wound repairing or healing emulsions, such as, for example, a water-based emulsion, optionally containing one or more of the following ingredients liquid paraffin, ethylene glycol monostearate, stearic acid, propylene glycol, paraffin wax, squalane, avocado oil, trolamine/sodium alginate, triethanolamine, cetyl palmitate, methylparaben (sodium salt), sorbic acid (as potassium salt), propylparaben (sodium salt), and/or fragrances (e.g., Biafine™ by Medix Pharmaceuticals Americas, Inc., Largo, Fla.).

Examples of suitable pain relievers and anti inflammatory agents include heparin, bromelain, ozone, analgesics, opioids, and acetaminophen. The pain relievers and anti-inflammatory agents may be included in the composition in an amount of from about 1% to about 25% of the composition depending on the type of wound and possibility of infection.

Examples of vitamin factors that may be used in the compositions of the invention or in combination therapy include Vitamin A and/or retinoids, Vitamin E, Vitamin C, Vitamin D, folic acid, vitamin B5, Bromelain, Vitamin B-complex, Zinc (oral and topical), Chondroitin sulfate (topical), Copper, Ornithine alpha-ketoglutarate (OKG), Arginine, Carnosine, chondroitin sulfate (oral), Glucosamine sulfate (oral), icthammol, calamine, silver sulphadiazine, chlorohexadine acetate, coal, tar. The vitamin factors may be included in the composition in an amount of from about 0.1% to about 25% of the composition.

Examples of minerals that may be used in the compositions of the invention include copper, magnesium, manganese, zinc, iron. The mineral factors may be included in the composition in an amount of from about 0.1% to about 25% of the composition.

The compounds and compositions will generally be stored in a container, such as a sealed container, or a water resistant sealed container.

Examples of herbal factors that may be used in the compositions of the invention include Aloe vera (topical), Chamomile (topical), Gotu kola (oral and topical), Honey (topical), Horse chestnut (topical), Arnica (topical), Bladderwrack (topical), Calendula (topical), Chaparral (topical), Comfrey (topical), Echinacea (topical), Horsetail (oral and topical), Plantain (topical), St. John's wart (topical), Tea tree oil (topical), goldenseal (topical), echinacea (topical), and Witch hazel (topical). The herbal factors may be included in the composition in an amount of from about 1 mg to about 6 mg and make up from about 0.1% to about 25% of the composition.

In another embodiment, anti-angiogenic compounds can be used for testing for pathologic angiogenesis and/or effectiveness of cancer drug candidate compounds or compositions for treating forms of cancer and/or allied cancer diseases. These anti-angiogenic compounds may advantageously be used to treat various types of vascularized cancers that progress and metastasize, including sarcomas (e.g., breast cancer), lymphomas and carcinomas (e.g., lung cancer), among other types of vascular tumor types. A further embodiment relates to the use of anti-angiogenic compounds for treating various types of ocular diseases (i.e., vision altering complications observed during diabetic retinopathy, choroidal neovascularization or age-related macular degeneration; ocular vascular proliferative lesions accompanying diabetes (diabetic retinopathy), choroidal neovascularization (CNV) or age-related macular degeneration (AMD)).

The present disclosure contains applications which may utilize both the peptides of the present disclosure and the anti-angiogenic compounds of the present disclosure. For example, a person may require administration of anti-angiogenic compounds to combat pancreatic cancer or glioblastoma, while requiring an intravitreal injection of humanized anti-angiogenic compound for treatment of wet AMD or diabetic retinopathy. At the same time, a diabetic patient may need local application of trace peptide levels for local promotion of wound healing angiogenesis and activation of nonhealing plantar ulcer into one that can heal and progress to wound closure. Upon completion of treatment, subsequently require administration of any combination of the peptides disclosed herein to reduce scarring.

Administration

A further embodiment of the present disclosure provides for the administration of, for example, the wound healing peptides, to a subject in need, by any suitable route including but not limited to, topically or by parenteral means, including subcutaneous and intramuscular injection, implantation of sustained release depots, intradermal injection, and the like. Any local administration is most useful for the embodiments of the disclosure. Topical formulations comprising the wound healing peptides include creams, ointments, aerosols, bandages and other advanced wound dressings, and the like.

Formulations of the present invention may be any that are appropriate for the route of administration and will be apparent to those skilled in the art. Accordingly, the composition of the present disclosure having a pharmaceutically- and/or physiologically-acceptable carrier, vehicle, or diluent. Such compositions of the present invention may be aqueous solutions, creams, emulsions, ointments, suspensions, gels, liposomal suspensions, and the like. Pharmaceutically acceptable carriers are well known in the art such as saline, and may also comprise bulking agents, other medicinal preparations, adjuvants and any other suitable pharmaceutical ingredients. Aqueous carriers can contain more than one buffer salt, as well as salts such as sodium and potassium chlorides, dextrose, polyethylene glycol and other solutes. One of skill in the art may also include suitable preservatives, antioxidants, stabilizers, antimicrobials, and buffering agents, for example, BHA, BHT, citric acid, ascorbic acid, and tetracycline.

Further, one may provide a peptide or anti-angiogenic compound of the present disclosure in solid form, particularly as a lyophilized powder. Lyophilized formulations generally contain stabilizing and bulking agents, such as human serum albumin, sucrose, and mannitol. As the skilled artisan will appreciate, the lyophilized powders may be reconstituted with any of the aforementioned diluents, carriers, and vehicles and used in the appropriate manner. The anti-angiogenic compound of the disclosure may be formed in a lyophilized solid for long-term storage, ease of use or transport, and the like. For example, when the lyophilized solid comprises the wound healing peptides of the disclosure, the lyophilized solid may be used under combat conditions as a solid for direct application to open wounds (i.e., sprinkle the powder into a wound). Another embodiment is directed to a reconstituted lyophilized powder comprising the anti-angiogenic compound that inhibits or reduces vascularization of cancer cells such as those found in tumors, where the lyophilized powder is reconstituted with a diluent for local injection.

The term "effective amount" refers to an amount of peptide or antisense oligonucleotide sufficient to exhibit a detectable therapeutic effect. The therapeutic effect may include, for example, without limitation, promoting the growth of tissue or cells curing the process of wound healing, promoting angiogenesis (neovascularization) in wound healing, inhibiting angiogenesis in cancerous cells, inhibiting angiogenesis in cancerous cells, tumors or macular degeneration, inhibition of tumor cell growth, and the like. The precise effective amount for administration to a subject will depend upon the subject's size and health, the nature and severity of the condition to be treated, and the like. The effective amount for a particular individual can be determined by routine experimentation based on the information provided herein and as calculated by the skilled practitioner based on dose response assays and animal models that correlate to human applications.

The term "pharmaceutically acceptable" refers to compounds, compositions, and carriers, vehicles, and diluents, which may be administered to mammals, including humans, without undue toxicity.

With regard to topical applications, peptides of the present disclosure will be utilized in effective amounts for the promotion of angiogenesis. For example, such effective amounts range from about subnanomolar to about micromolar, preferably from about 0.5 nM to about 250 nM, and most advantageously from about 10 nM to about 100 nM. The effective amounts range from about $6\times10^{-10}$% to about $6\times10^{-6}$% of the weight of the subject. For internal use, the formulation may be released directly into the region to be treated either from implanted slow release polymeric material or from slow release pumps or repeated injections. The release rate in either case is about 100 ng to about 100 mg/day/cm$^3$.

Systemic dosages of anti-angiogenic compounds generally depend on the age, weight and conditions of the patient and on the administration route.

The content of all patents, patent applications, published articles, abstracts, books, reference manuals and abstracts, as cited herein are hereby incorporated by reference in their entireties to more fully describe the state of the art to which the disclosure pertains.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variations that fall within the scope of the appended claims.

EXAMPLES

The following Examples further describe and demonstrate embodiments within the scope of the present disclosure. The examples are given solely for the purpose of illustration and are not to be constructed as limitations of the present disclosure, as many variations thereof are possible without departing from the spirit and scope of the disclosure.

Example 1

Crude raw lyophilized pooled human-platelet rich plasma, prepared in accordance with the procedures disclosed in Gandy U.S. Patent Publication No. 20060142198 and Gandy U.S. Patent Publication No. 20060004189, was obtained. The crude material was treated, biochemically separated, and enriched by size exclusion and ion exchange chromatography DEA Cellulose to produce a fraction having enriched activity. Tandem Mass Spectrometry (MS/MS) combined with database searching was employed to identify the components contained in a sample of the raw material. Two unnamed peptide sequences, SEQ ID NO: 1 and SEQ ID NO: 2, were identified and selected for investigation.

The peptides identified were then synthesized at the Tufts University Core Facility using an ABI 431 Peptide Synthesizer employing FastMoc Chemistry. The isolated and purified peptides were then re-characterized by Mass Spectrometry analysis and analytical HPLC chromatography. The two peptide sequences, SEQ ID NO: 1 and SEQ ID NO: 2, were then combined to form a new peptide, i.e., SEQ ID NO: 3.

Example 2

Each of the three peptide sequences were then analyzed for activity via (1) in vitro angiogenesis assays where blood vessel formation in vitro was quantified; (2) in vitro response to injury analyses, including quantitative analysis, of migration in response to injury; and (3) in vitro quantitation of cell proliferation assays. The results of experiments performed are illustrated in FIGS. 1 to 4.

Figure 2:
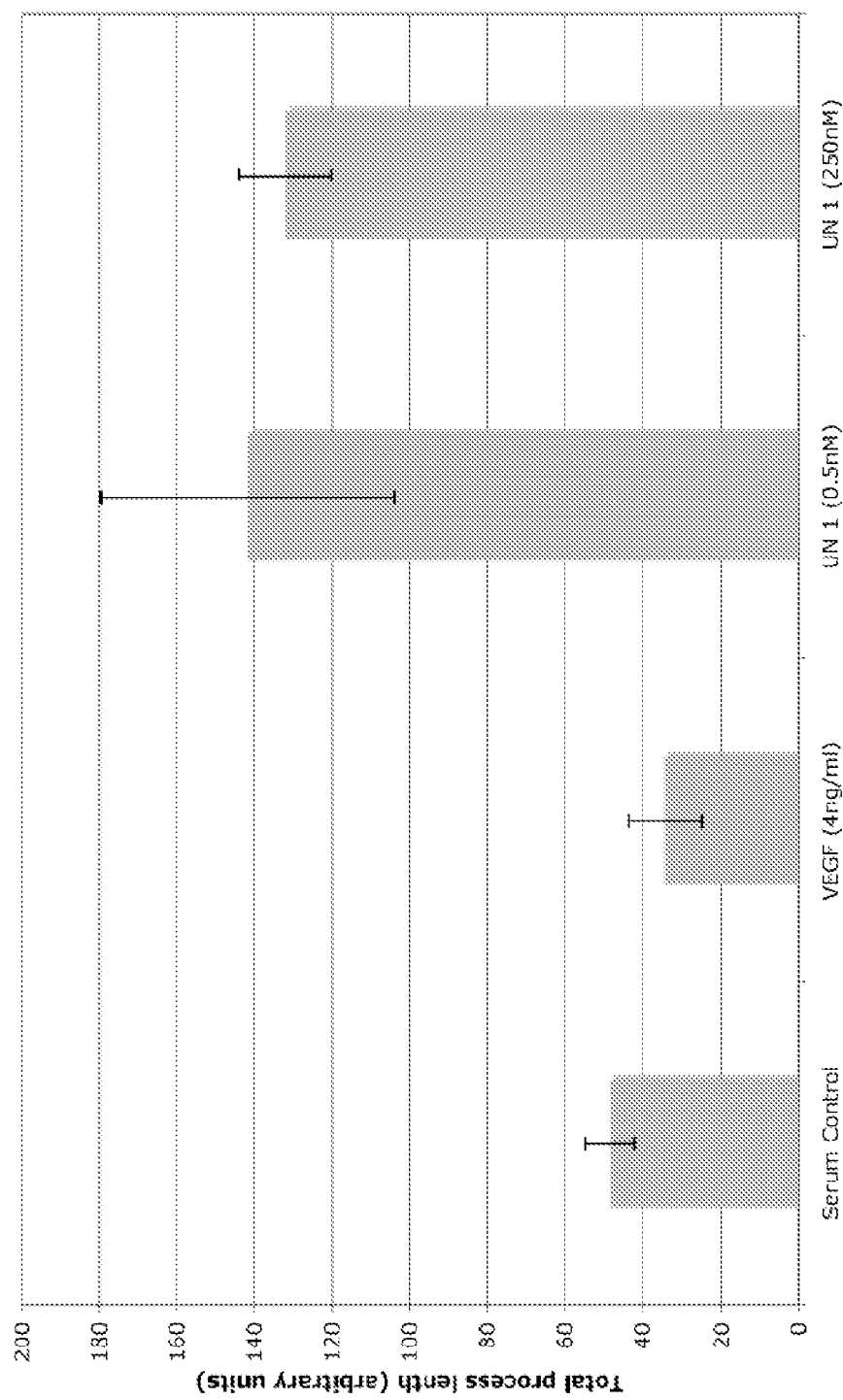
FIG. 2 is a graph illustrating a measure of angiogenesis in terms of total process length in Human Microvascular Endothelial Cells (HMVEC) with 0.4 nM and 250 nM of the SEQ ID NO: 1 ("UN1").

The peptide (SEQ. ID NO: 1 ("UN1")) was compared to each of VEGF 4 ng/ml and Serum Control in an in vitro angiogenesis analysis. As illustrated in FIGS. 1 and 2, the peptide of the invention induced significant tubule formation and process length in comparison to the Serum Control and VEGF.

Figure 3:
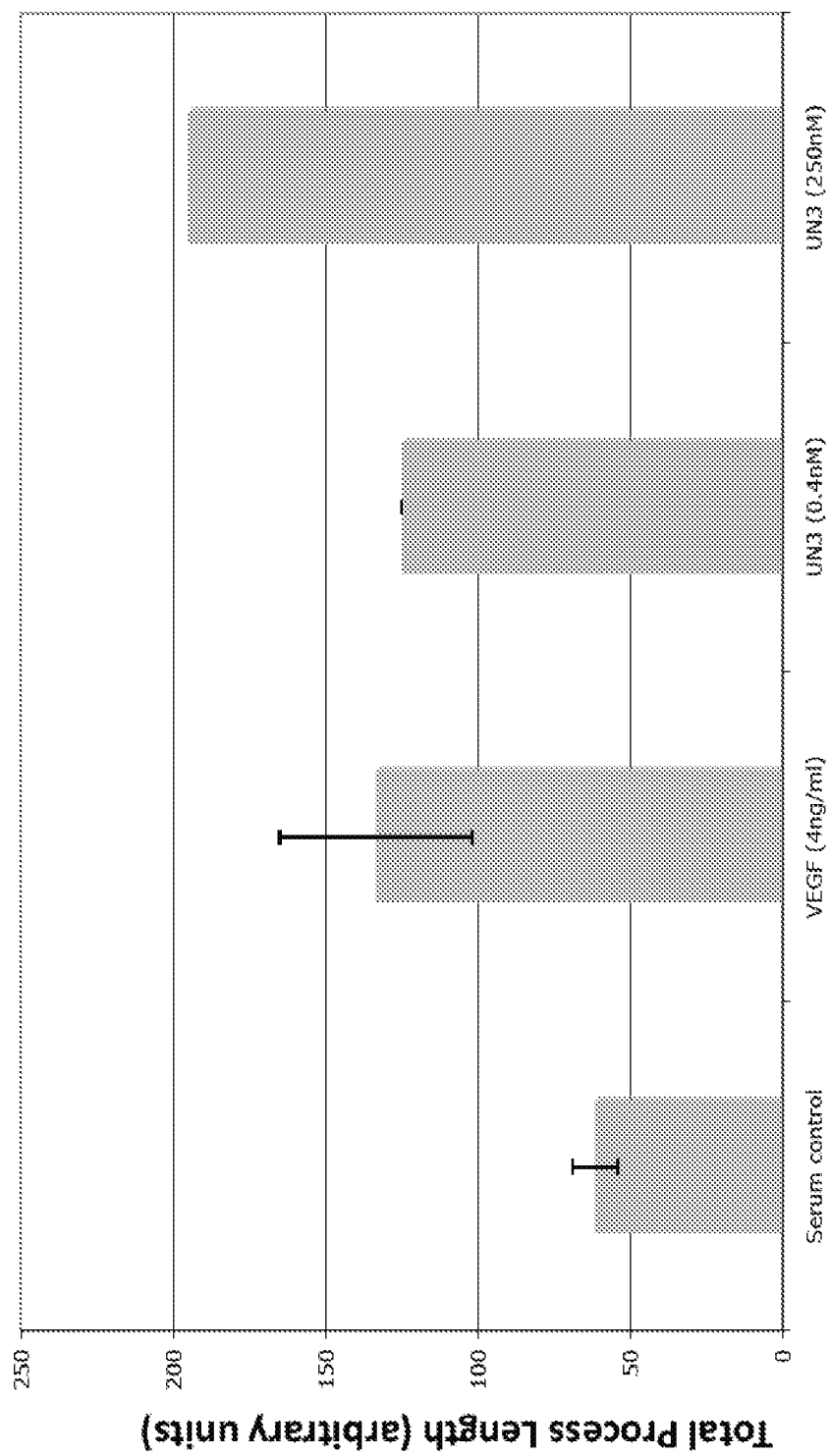
FIG. 3 is a graph illustrating a measure of angiogenesis in terms of total process length in Human Microvascular Endothelial Cells (HMVEC) with 0.4 nM and 250 nM of the peptide of SEQ ID NO: 3 ("UN3").

The peptide (SEQ ID NO: 3 ("UN3")) was also compared to VEGF and Serum Control in in vitro angiogenesis analysis. As illustrated in FIG. 3, the peptide of the invention showed a significant increase in process length in comparison with Serum Control. It also showed a significant increase in process length in comparison to VEGF at an amount of 250 nM.

Figure 4:
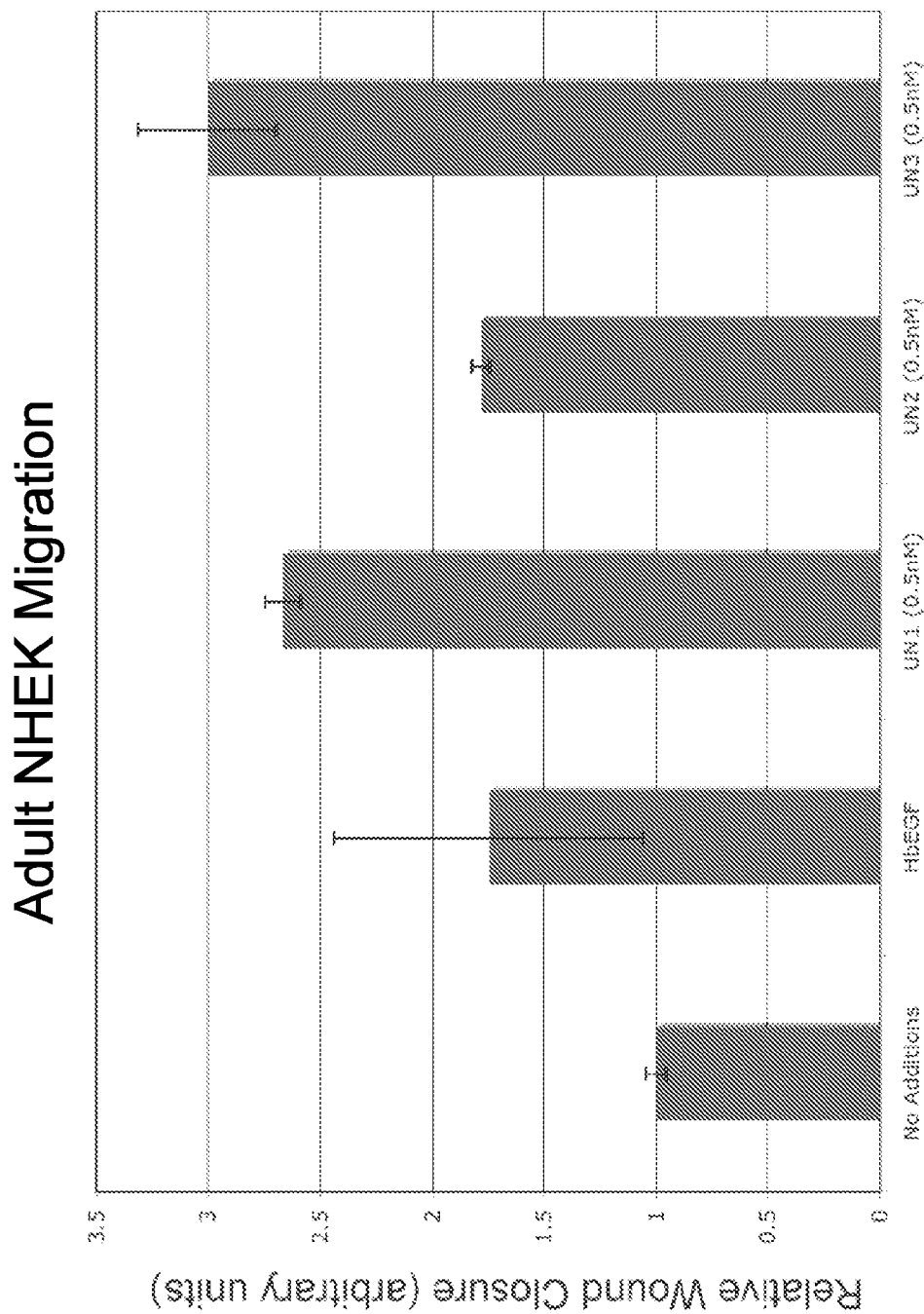
FIG. 4 is a graph illustrating a measure of relative wound closure via Normal Human Epithelial Keratinocyte (NHEK) migration after exposure to 0.5 nM of each of the peptides of SEQ ID NOs: 1, 2, and 3 ("UN1," "UN2," and "UN3" respectively). The relative wound closure was significantly better for each of the peptides compared to "control."

In addition, each of the three peptides of the invention were compared with regard to adult normal human epithelial keratinocyte migration. As illustrated in FIG. 4, each performed substantially better than the control.

What is claimed:

1. An isolated peptide comprising SEQ ID NO: 1.

2. The isolated peptide of claim 1, wherein the isolated peptide consists of SEQ ID NO: 1.

3. An isolated peptide comprising SEQ ID NO: 3.

4. The isolated peptide of claim 3, wherein the isolated peptide consists of SEQ ID NO: 3.

5. An isolated polynucleotide encoding a peptide comprising SEQ ID NO: 1.

6. The isolated polynucleotide of claim 5, wherein the isolated polynucleotide encodes a peptide consisting of SEQ ID NO: 1.

7. An isolated polynucleotide encoding a peptide comprising SEQ ID NO: 3.

8. The isolated polynucleotide of claim 7, wherein the isolated polynucleotide encodes a peptide consisting of SEQ ID NO: 3.

9. An isolated polynucleotide fully complementary to an isolated polynucleotide encoding a peptide comprising SEQ ID NO: 1.

10. The isolated polynucleotide of claim 9, wherein the peptide consists of SEQ ID NO: 1.

11. An isolated polynucleotide fully complementary to an isolated polynucleotide encoding a peptide comprising SEQ ID NO: 3.

12. The isolated polynucleotide of claim 11, wherein the peptide consists of SEQ ID NO: 3.

13. A vector comprising an isolated polynucleotide encoding a peptide comprising SEQ ID NO: 1.

14. The vector of claim 13, wherein the peptide consists of SEQ ID NO: 1.

15. A vector comprising an isolated polynucleotide encoding a peptide comprising SEQ ID NO: 3.

16. The vector of claim 15, wherein the peptide consists of SEQ ID NO: 3.

17. A composition comprising an isolated peptide comprising SEQ ID NO: 1, and a carrier, vehicle, or diluent.

18. The composition of claim 17, wherein the isolated peptide consists of SEQ ID NO: 1.

19. A composition comprising an isolated peptide comprising SEQ ID NO: 3, and a carrier, vehicle, or diluent.

20. The composition of claim 19, wherein the isolated peptide consists of SEQ ID NO: 3.

21. A kit, comprising:
(1) an isolated peptide selected from the group consisting of (a), (b), (c), and (d):
   a. an isolated peptide comprising SEQ ID NO: 1;
   b. an isolated peptide comprising SEQ ID NO: 3;
   c. an isolated peptide consisting of SEQ ID NO: 1;
   d. an isolated peptide consisting of SEQ ID NO: 3; or
(2) an isolated polynucleotide selected from the group consisting of (e), (f), (g), and (h):
   e. an isolated polynucleotide encoding a peptide comprising SEQ ID NO: 1;
   f. an isolated polynucleotide encoding a peptide comprising SEQ ID NO: 3;
   g. an isolated polynucleotide encoding a peptide consisting of SEQ ID NO: 1;
   h. an isolated polynucleotide encoding a peptide consisting of SEQ ID NO: 3; or
(3) an isolated polynucleotide selected from the group consisting of (i), (j), (k), and (l):
   i. an isolated polynucleotide fully complementary to an isolated polynucleotide encoding a peptide comprising SEQ ID NO: 1;
   j. an isolated polynucleotide fully complementary to an isolated polynucleotide encoding a peptide comprising SEQ ID NO: 3;
   k. an isolated polynucleotide fully complementary to an isolated polynucleotide encoding a peptide consisting of SEQ ID NO: 1;
   l. an isolated polynucleotide fully complementary to an isolated polynucleotide encoding a peptide consisting of SEQ ID NO: 3.

* * * * *

SEQUENCE LISTING

```
<160> NUMBER OF SEQ ID NOS: 17

<210> SEQ ID NO 1
<211> LENGTH: 9
<212> TYPE: PRT
<213> ORGANISM: Homo sapiens

<400> SEQUENCE: 1

Glu Leu Leu Glu Ser Tyr Ile Asp Arg
1               5

<210> SEQ ID NO 2
<211> LENGTH: 13
<212> TYPE: PRT
<213> ORGANISM: Homo sapiens

<400> SEQUENCE: 2

Thr Ala Thr Ser Glu Tyr Gln Thr Phe Phe Asn Pro Arg
1               5                   10

<210> SEQ ID NO 3
<211> LENGTH: 23
<212> TYPE: PRT
<213> ORGANISM: Homo sapiens

<400> SEQUENCE: 3

Glu Leu Leu Glu Ser Tyr Ile Asp Arg Pro Thr Ala Thr Ser Glu Tyr
1               5                   10                  15

Gln Thr Phe Phe Asn Pro Arg
            20

<210> SEQ ID NO 4
<211> LENGTH: 23
<212> TYPE: PRT
<213> ORGANISM: Homo sapiens

<400> SEQUENCE: 4

Thr Ala Thr Ser Glu Tyr Gln Thr Phe Phe Asn Pro Arg Pro Glu Leu
1               5                   10                  15

Leu Glu Ser Tyr Ile Asp Arg
            20
```

```
<210> SEQ ID NO 5
<211> LENGTH: 27
<212> TYPE: DNA
<213> ORGANISM: Homo sapiens

<400> SEQUENCE: 5
gaacttcttg aatcttatat tgatcgt                                    27

<210> SEQ ID NO 6
<211> LENGTH: 27
<212> TYPE: DNA
<213> ORGANISM: Homo sapiens

<400> SEQUENCE: 6
gagttcttcg agagctacat cgacagc                                    27

<210> SEQ ID NO 7
<211> LENGTH: 27
<212> TYPE: DNA
<213> ORGANISM: Homo sapiens

<400> SEQUENCE: 7
gaactactag aatcatatat agatcga                                    27

<210> SEQ ID NO 8
<211> LENGTH: 27
<212> TYPE: DNA
<213> ORGANISM: Homo sapiens

<400> SEQUENCE: 8
gaactgctgg aatcgtatat tgatcgg                                    27

<210> SEQ ID NO 9
<211> LENGTH: 39
<212> TYPE: DNA
<213> ORGANISM: Homo sapiens

<400> SEQUENCE: 9
actgctactt ctgaatatca aactttttt aatcctcgt                        39

<210> SEQ ID NO 10
<211> LENGTH: 39
<212> TYPE: DNA
<213> ORGANISM: Homo sapiens

<400> SEQUENCE: 10
accgccacca gcgagtacca gaccttcttc aaccccagc                       39

<210> SEQ ID NO 11
<211> LENGTH: 39
<212> TYPE: DNA
<213> ORGANISM: Homo sapiens

<400> SEQUENCE: 11
acagcaacat cagaatatca aacattttt aatccacga                        39

<210> SEQ ID NO 12
<211> LENGTH: 39
<212> TYPE: DNA
<213> ORGANISM: Homo sapiens

<400> SEQUENCE: 12
acggcgacgt cggaatatca aacgttttt aatccgcgg                        39
```

```
<210> SEQ ID NO 13
<211> LENGTH: 69
<212> TYPE: DNA
<213> ORGANISM: Homo sapiens

<400> SEQUENCE: 13
gaacttcttg aatcttatat tgatcgtcct actgctactt ctgaatatca aactttttt      60 aatcctcgt                                                              69

<210> SEQ ID NO 14
<211> LENGTH: 69
<212> TYPE: DNA
<213> ORGANISM: Homo sapiens

<400> SEQUENCE: 14
gagttcttcg agagctacat cgacagcccc accgccacca gcgagtacca gaccttcttc      60
aaccccagc                                                              69

<210> SEQ ID NO 15
<211> LENGTH: 69
<212> TYPE: DNA
<213> ORGANISM: Homo sapiens

<400> SEQUENCE: 15
gaactactag aatcatatat agatcgacca acagcaacat cagaatatca aacatttttt      60
aatccacga                                                              69

<210> SEQ ID NO 16
<211> LENGTH: 69
<212> TYPE: DNA
<213> ORGANISM: Homo sapiens

<400> SEQUENCE: 16
gaactgctgg aatcgtatat tgatcggccg acggcgacgt cggaatatca aacgttttt       60 aatccgcgg                                                              69

<210> SEQ ID NO 17
<211> LENGTH: 39
<212> TYPE: DNA
<213> ORGANISM: Artificial Sequence
<220> FEATURE:
<223> OTHER INFORMATION: Synthetic Sequence of a KpnI site, a Kozak
      consensus site, and a region targeting a myc sequence.

<400> SEQUENCE: 17
gcggttacca ccaccatgga acaaaaactc atctcagaa                             39
```